United States Patent
Takei

(10) Patent No.: US 9,211,057 B2
(45) Date of Patent: Dec. 15, 2015

(54) IMAGE PICKUP SYSTEM AND ENDOSCOPE SYSTEM

(75) Inventor: Shunji Takei, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 1282 days.

(21) Appl. No.: 13/031,946

(22) Filed: Feb. 22, 2011

(65) Prior Publication Data

US 2011/0152614 A1    Jun. 23, 2011

Related U.S. Application Data

(63) Continuation of application No. PCT/JP2009/052771, filed on Feb. 18, 2009.

(30) Foreign Application Priority Data

Aug. 22, 2008 (JP) ................................ 2008-214162

(51) Int. Cl.
*A61B 1/05* (2006.01)
*A61B 1/07* (2006.01)
*A61B 1/04* (2006.01)
(Continued)

(52) U.S. Cl.
CPC .............. *A61B 1/05* (2013.01); *A61B 1/00009* (2013.01); *A61B 1/04* (2013.01); *A61B 1/041* (2013.01); *A61B 1/043* (2013.01); *A61B 1/0638* (2013.01); *A61B 1/0646* (2013.01);
(Continued)

(58) Field of Classification Search
CPC .................... A61B 1/00009; A61B 1/04–1/05; A61B 1/43; G06T 2207/10068
USPC .......................................... 600/109, 110, 160
See application file for complete search history.

(56) References Cited

U.S. PATENT DOCUMENTS 6,364,829 B1    4/2002  Fulghum
2002/0138008 A1*  9/2002  Tsujita et al. ................. 600/473

FOREIGN PATENT DOCUMENTS

JP    2001-224549       8/2001
JP    2001-258820 A     9/2001

OTHER PUBLICATIONS

JP 2001-224549, Pub. Date Aug. 21, 2001, Inventor: Kazuo et al. Applicant: Fuji Photo Film Cc LTD.*
European Search Report dated Nov. 7, 2012 from corresponding European Patent Application No. EP 09 80 8096.3.
(Continued)

*Primary Examiner* — Anhtuan T Nguyen
*Assistant Examiner* — Rajaa El Alami
(74) *Attorney, Agent, or Firm* — Scully, Scott, Murphy & Presser, P.C.

(57) ABSTRACT

An image pickup system of the present invention has a light emitting section that emits a first illuminating light and a second illuminating light to an object, an image pickup section that picks up an image of a first return light and an image of a second return light, and outputs the images as image pickup signals respectively, an image generating section that generates a first image and a second image respectively based on the image pickup signals, a differential value calculating section that calculates a first differential value corresponding to the first image and a second differential value corresponding to the second image respectively, a calculation section that performs calculation processing by using the first differential value and the second differential value, and a region discriminating section that discriminates between regions in the object by applying threshold processing to a calculation result of the calculation section.

3 Claims, 5 Drawing Sheets

(51) Int. Cl.
*A61B 1/06* (2006.01)
*A61B 1/00* (2006.01)

(52) U.S. Cl.
CPC ............... *A61B 1/0669* (2013.01); *A61B 1/07* (2013.01); *G06T 2207/10068* (2013.01)

(56) References Cited

OTHER PUBLICATIONS

International Search Report dated May 19, 2009.

\* cited by examiner

• : VALUE OF VECTOR

× : ABNORMAL REGION
○ : NORMAL REGION OR BOUNDARY PORTION BY ILLUMINATION INTENSITY DISTRIBUTION

IMAGE PICKUP SYSTEM AND ENDOSCOPE SYSTEM

CROSS REFERENCE TO RELATED APPLICATION

This application is a continuation application of PCT/JP2009/052771 filed on Feb. 18, 2009 and claims benefit of Japanese Application No. 2008-214162 filed in Japan on Aug. 22, 2008, the entire contents of which are incorporated herein by this reference.

BACKGROUND OF THE INVENTION

1. Field of the Invention

The present invention relates to an image pickup system and an endoscope system, and particularly relates to an image pickup system and an endoscope system which are capable of discriminating between a predetermined region and a region other than the predetermined region in an object.

2. Description of the Related Art

Endoscope apparatuses, which acquire the images of an object in a test subject and can generate images corresponding to the images of the object, have been conventionally used widely in the medical field and the like. In particular, the endoscope apparatuses in the medical field are mainly used by surgeons for the purpose of performing treatment such as inspection and observation of the insides of living bodies.

As modes of observation using the endoscope apparatuses in the medical field which are generally known, there are for example, auto fluorescence observation in which the object inside a living body is irradiated with an excitation light and a reference light having specific wavelength bands, and a fluorescence image as an image of auto fluorescence emitted from the object in response to the excitation light, and a reference light image as the image of a reflection light which is the reference light reflected in the object are acquired, in addition to white color light observation in which the object in a living body is irradiated with a white color light, and a white color light image as the image of the object substantially similar to observation by naked eyes is acquired. As an apparatus capable of performing such auto fluorescence observation, for example, the endoscopic image acquiring apparatus described in Japanese Patent Application Laid-Open Publication No. 2001-224549 is cited.

Meanwhile, in the purpose of making it easy to find a lesion with less visibility in the white color light image, an endoscope apparatus has been proposed in recent years which can output a superimposed image with the biological information obtained from a fluorescence image and a reference light image superimposed on a white color light image.

Further, in the observation using such a superimposed image, a method is proposed which calculates the ratio of the gradation value of the reference light image to the gradation value of the fluorescence image, acquires the information of the region where a lesion is present by applying threshold processing to the calculation result, and thereafter, superimposes the information on a white color light image.

SUMMARY OF THE INVENTION

An image pickup system in the present invention has a light emitting section that emits a first illuminating light and a second illuminating light to an object, an image pickup section that picks up an image of a first return light from the object corresponding to the first illuminating light and an image of a second return light from the object corresponding to the second illuminating light, and outputs the images as image pickup signals respectively, an image generating section that generates a first image corresponding to the first return light and a second image corresponding to the second return light respectively based on the image pickup signals, a differential value calculating section that calculates a first differential value corresponding to the first image and a second differential value corresponding to the second image respectively, a calculation section that performs calculation processing by using the first differential value and the second differential value, and a region discriminating section that discriminates between a predetermined region and a region other than the predetermined region in the object by applying threshold processing to a calculation result of the calculation section.

An endoscope system in the present invention has a light source apparatus that emits an excitation light and a reference light to a biological tissue, an endoscope including an image pickup device that picks up images of reflection lights, which are fluorescence emitted from the biological tissue in response to the excitation light, and the reference light that are reflected in the biological tissue, and outputs the images as image pickup signals respectively, an image generating section that generates a fluorescence image corresponding to the fluorescence, and a reference light image corresponding to the reflection light respectively based on the image pickup signals, a differential value calculating section that calculates a fluorescence differential value as a differential value corresponding to the fluorescence image, and a reference light differential value as a differential value corresponding to the reference light image respectively, a calculation section that performs calculation processing by using the fluorescence differential value and the reference light differential value, and a region discriminating section that discriminates between an abnormal region and a normal region in the biological tissue by applying threshold processing to a calculation result of the calculation section.

DETAILED DESCRIPTION OF THE PREFERRED EMBODIMENT(S)

Hereinafter, an embodiment of the present invention will be described with reference to the drawings.

Figure 1:
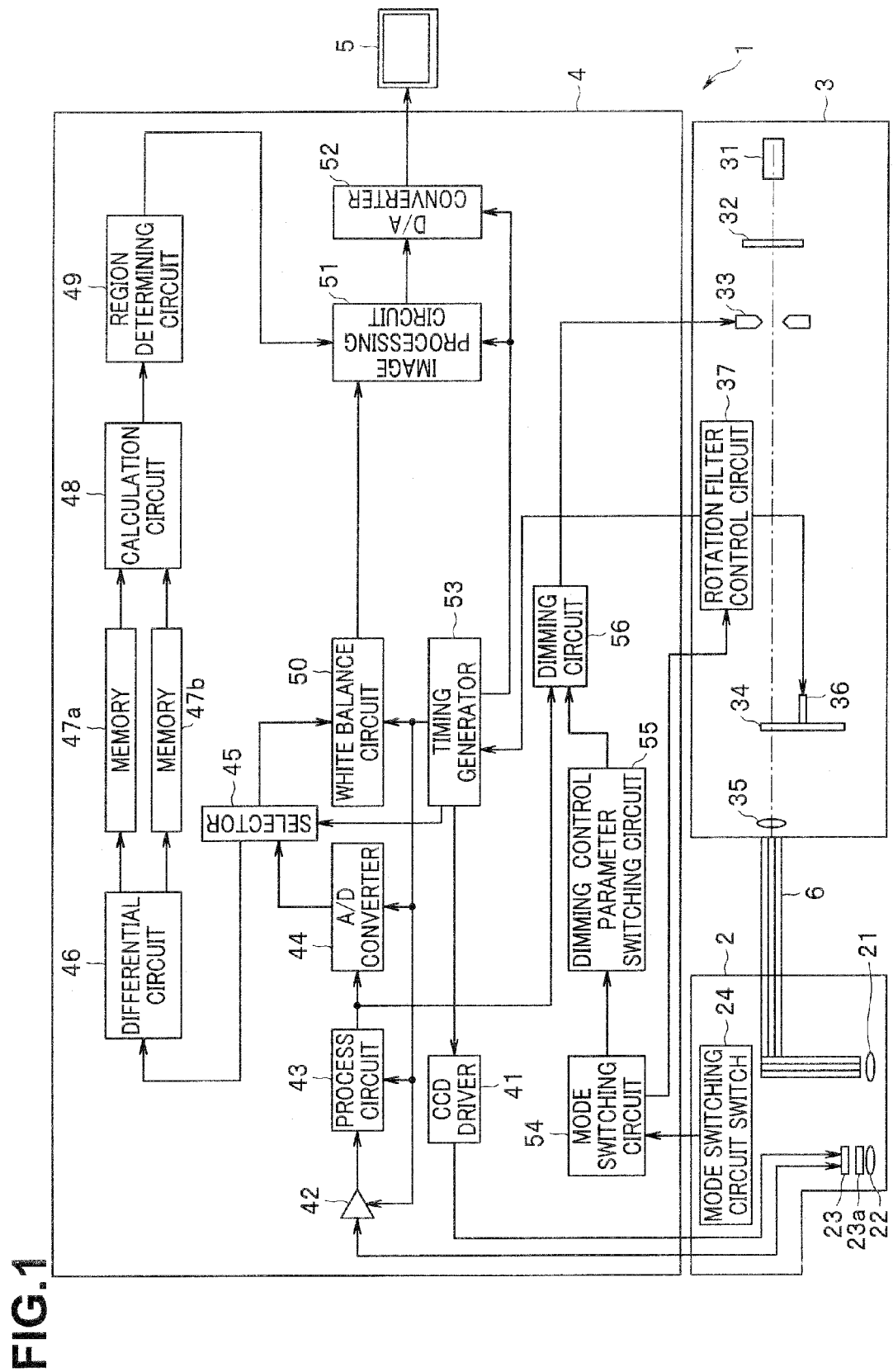
FIG. 1 is a diagram showing one example of a configuration of principal parts of an endoscope system according to the present embodiment.
Figure 2:
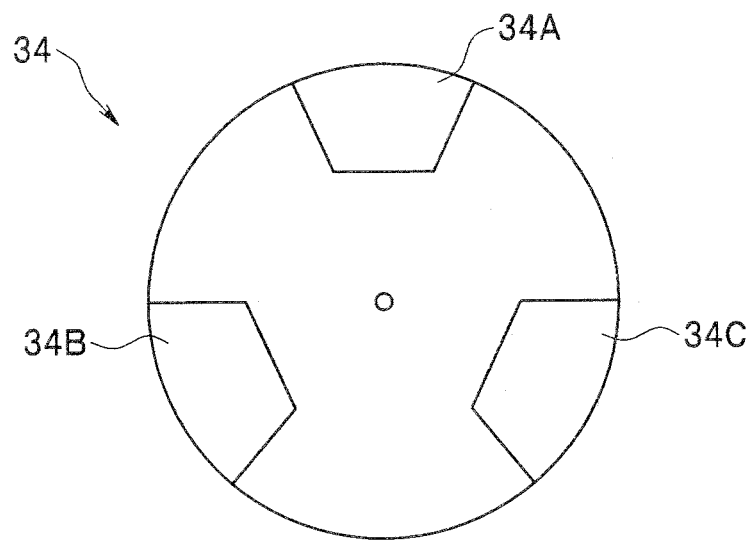
FIG. 2 is a view showing one example of a configuration of a rotation filter provided at a light source apparatus of FIG. 1.
Figure 3:
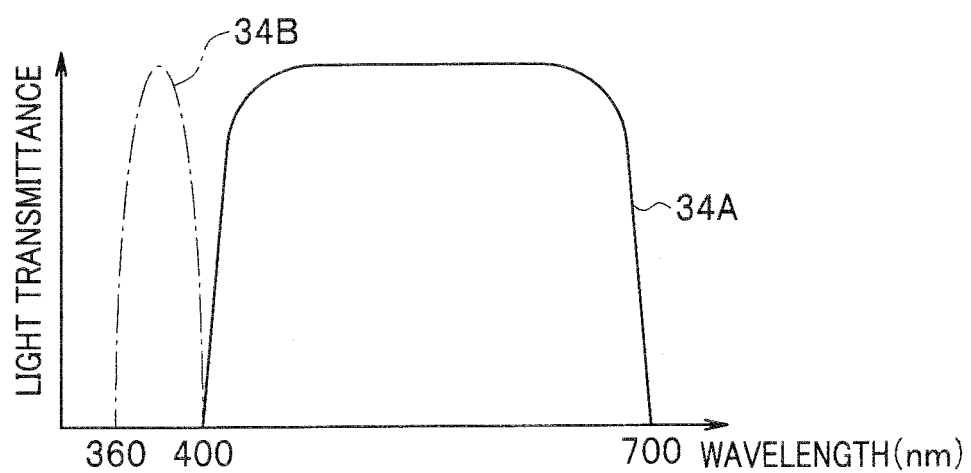
FIG. 3 is a diagram showing one example of spectral characteristics of a white color light filter and an excitation light filter which are provided at the rotation filter of FIG. 2.
Figure 4:
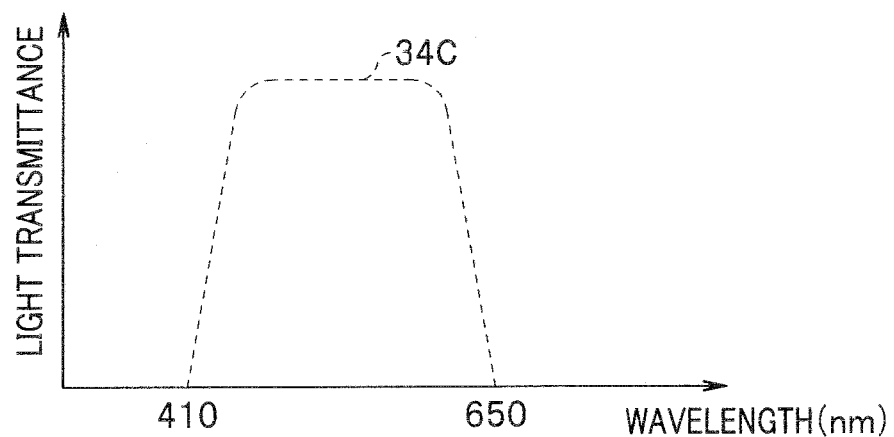
FIG. 4 is a diagram showing one example of a spectral characteristic of a reference light filter provided at the rotation filter of FIG. 2.
Figure 5:
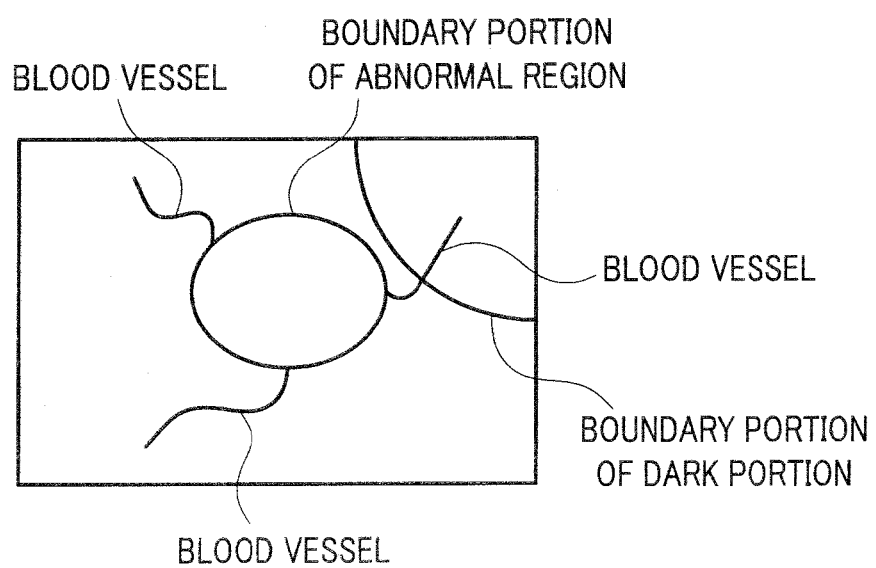
FIG. 5 is a view showing one example of a fluorescence differential value generated by a processor of FIG. 1.
Figure 6:
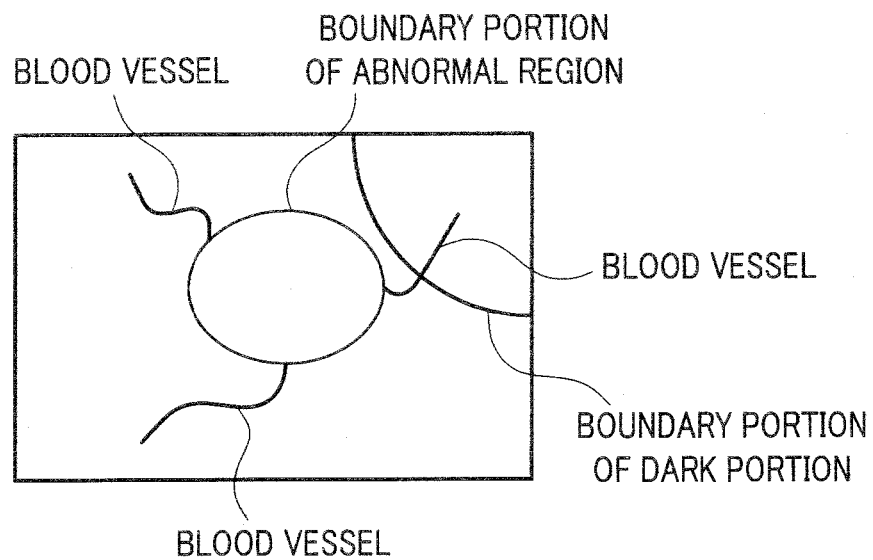
FIG. 6 is a view showing one example of a reference light differential value generated by the processor of FIG. 1.
Figure 7:
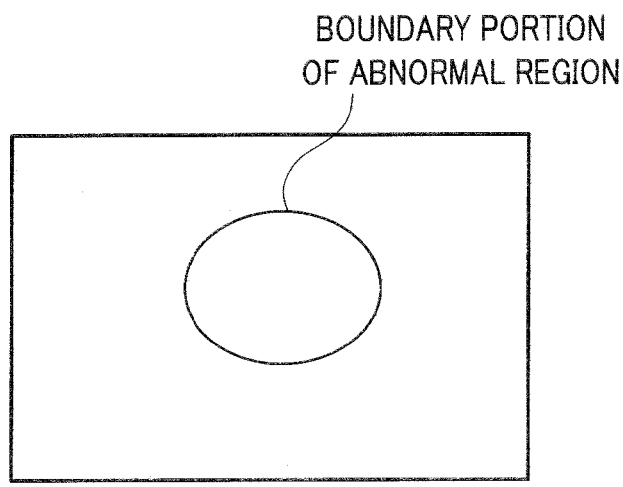
FIG. 7 is a view showing one example of a determination target image generated by using the fluorescence differential value of FIG. 5 and the reference light differential value of FIG. 6.
Figure 8:
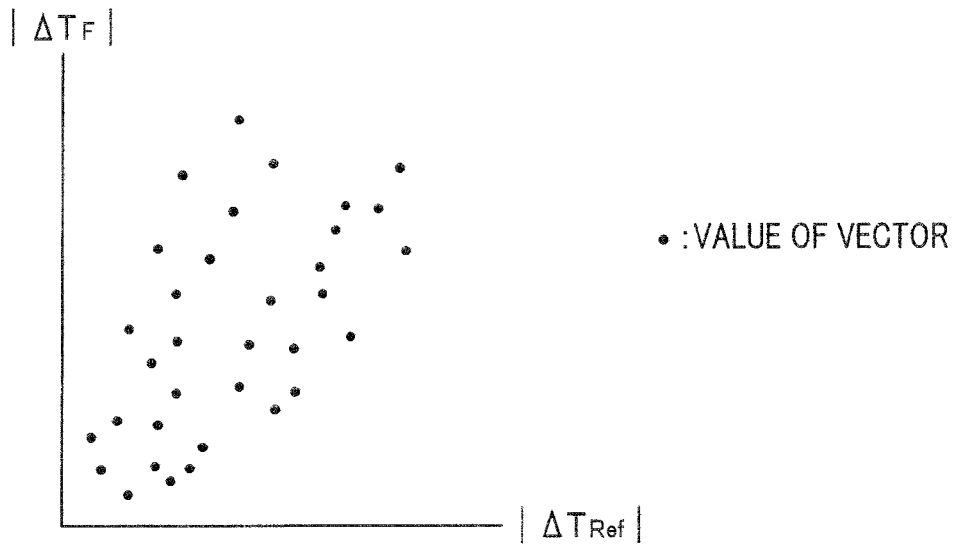
FIG. 8 is a diagram showing one example of two-dimensional scatter data generated by the processor of FIG. 1.
Figure 9:
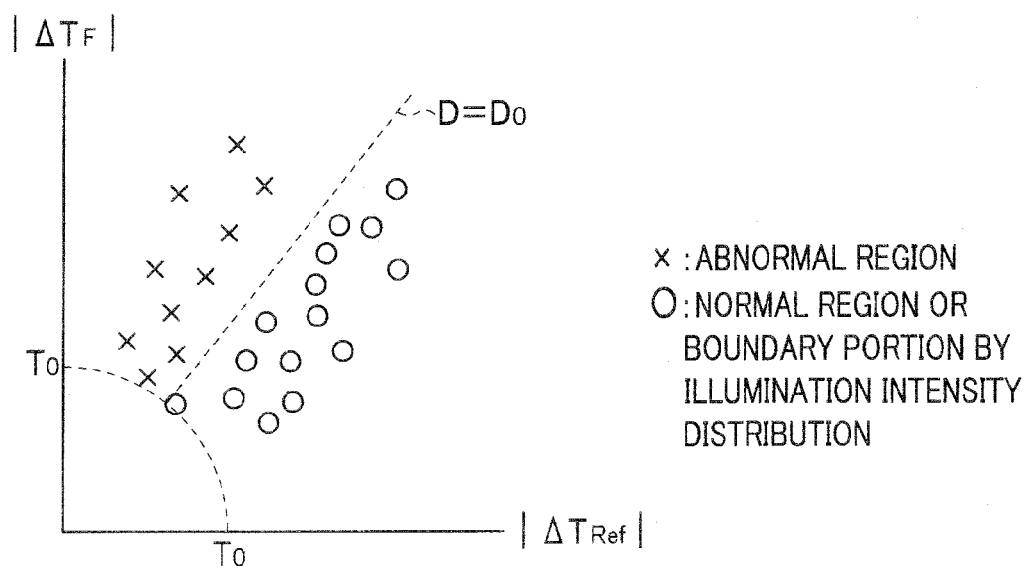
FIG. 9 is a diagram showing one example of a discrimination result based on the two-dimensional scatter data of FIG. 8.

FIGS. 1 to 9 relate to the embodiment of the present invention. FIG. 1 is a diagram showing one example of a configuration of principal parts of an endoscope system according to the present embodiment. FIG. 2 is a view showing one example of a configuration of a rotation filter provided at a light source apparatus of FIG. 1. FIG. 3 is a diagram showing one example of spectral characteristics of a white color light filter and an excitation light filter which are provided at the rotation filter of FIG. 2. FIG. 4 is a diagram showing one example of a spectral characteristic of a reference light filter provided at the rotation filter of FIG. 2. FIG. 5 is a view showing one example of a fluorescence differential value generated by a processor of FIG. 1, FIG. 6 is a view showing one example of a reference light differential value generated by the processor of FIG. 1, FIG. 7 is a view showing one example of a determination target image generated by using the fluorescence differential value of FIG. 5 and the reference light differential value of FIG. 6. FIG. 8 is a diagram showing one example of two-dimensional scatter data generated by the processor of FIG. 1. FIG. 9 is a diagram showing one example of a discrimination result based on the two-dimensional scatter data of FIG. 8.

An endoscope system 1 as an image pickup system of the present embodiment is configured by having, as principal parts, an endoscope 2 which can be inserted into a living body, picks up an image of an object such as a biological tissue present inside the living body, and outputs the image of the biological tissue as an image pickup signal, a light source apparatus 3 which supplies an illuminating light for illuminating the object to the endoscope 2 through a light guide 6 inserted through the endoscope 2, a processor 4 which performs signal processing corresponding to the image pickup signal outputted from the endoscope 2, and outputs the image pickup signal after being objected to the signal processing as a video signal, and a monitor 5 which displays the image of the object picked up by the endoscope 2 as an image based on the video signal outputted from the processor 4, as shown in FIG. 1.

The endoscope 2 is configured by having an illumination optical system 21 which emits an illuminating light supplied from the light source apparatus 3 and is transmitted by the light guide 6, an objective optical system 22 which forms the image of the object illuminated by the illuminating light emitted from the illumination optical system 21, a CCD (charge coupled device) 23 which is disposed at the image forming position of the objective optical system 22, an excitation light cut filter 23a disposed at the front stage of the CCD 23, and a mode switching instruction switch 24 which performs switching of the observation mode in the endoscope system 1.

The CCD 23 as an image pickup section is configured by including a primary color mosaic filter or a complementary color mosaic filter on its own image pickup surface.

The excitation light cut filter 23a is configured as an optical device which is set so that the transmittance of the wavelength band of an excitation light which will be described later becomes substantially zero.

The mode switching instruction switch 24 outputs an instruction signal for switching the observation mode in the endoscope system 1 to any one of a white color light observation mode or a fluorescence observation mode according to the operation by the surgeon or the like. The details of the white color light observation mode and the fluorescence observation mode will be described later.

The light source apparatus 3 as a light emission section has a lamp 31, a heat radiation cut filter 32 which cuts off the heat radiation of the white color light emitted by the lamp 31, a diaphragm apparatus 33, a rotation filter 34 which makes the white color light passing through the diaphragm apparatus 33 the illuminating light corresponding to the observation mode of the endoscope system 1, a condensing optical system 35 which gathers the illuminating light passing through the rotation filter 34 and emits the illuminating light to the light guide 6, a rotation filter motor 36 which rotationally drives the rotation filter 34, and a rotation filter control circuit 37.

The lamp 31 is configured by, for example, a xenon lamp or the like, which is a light source capable of emitting a white color light.

The diaphragm apparatus 33 regulates the light amount of the illuminating light passing through the heat radiation cut filter 32 based on the diaphragm control signal outputted from the processor 4.

The rotation filter 34 is configured to be disk-shaped with the center as the rotating axis as shown in FIG. 2. Further, the rotation filter 34 is configured by having a white color light filter 34A, an excitation light filter 34B and a reference light filter 34C which are respectively provided along a circumferential direction at an outer circumferential side as shown in FIG. 2.

The white color light filter 34A is formed to transmit lights in the wavelength bands of a red color, a green color and a blue color. In concrete, the white color light filter 34A is formed to transmit the light in the wavelength band of 400 nm to 700 nm inclusive as shown in FIG. 3, for example. More specifically, the light emitted from the lamp 31 becomes a white color light including the wavelength band of 400 nm to 700 inclusive by passing through the white color light filter 34A.

The excitation light filter 34B includes an excitation wavelength capable of causing fluorescence to be generated by irradiation to a living body, and is formed so as to transmit the light in the wavelength band which does not overlap the transmission band of the white color light filter 34A. In concrete, the excitation light filter 34B is formed to transmit the light in the wavelength band of 360 nm to less than 400 nm, as shown in FIG. 3, for example. More specifically, the light emitted from the lamp 31 becomes the excitation light including the wavelength band of 360 nm to less than 400 nm by passing through the excitation light filter 34B.

The reference light filter 34C is formed to transmit the light in the wavelength band substantially the same as the fluorescence emitted from a living body. In concrete, the reference light filter 34C is formed to transmit the light in the wavelength band of 410 nm to 650 nm inclusive as shown in, for example, FIG. 4. More specifically, the light emitted from the lamp 31 becomes the reference light including the wavelength band of 410 nm to 650 nm inclusive by passing thorough the reference light filter 34C.

The rotation filter control circuit 37 controls rotational drive of the rotation filter motor 36 based on the observation mode switching signal outputted from the processor 4, and outputs a synchronous signal synchronized with the rotation of the rotation filter 34 to the processor 4.

As a result that the respective sections of the light source apparatus 3 have the configurations as described above, the white color light which has passed through the white color light filter 34A, the excitation light which has passed through the excitation light filter 34B, and the reference light which has passed through the reference light filter 34C are respectively gathered by the condensing optical system 35 as the frame-sequential illuminating light, and thereafter, are emitted to the light guide 6.

The processor 4 has a CCD driver 41 which drives the CCD 23, an amplifier 42 which amplifies the image pickup signal outputted from the CCD 23, a process circuit 43 which applies processing such as correlated double sampling to the image pickup signal outputted from the amplifier 42, and an A/D converter 44 which converts the image pickup signal outputted from the process circuit 43 into a digital image signal, as shown in FIG. 1. The CCD driver 41, the amplifier 42, the process circuit 43 and the A/D converter 44 operate in response to the timing signals from a timing generator 53. Further, an image generating section in the present embodiment is configured by including the amplifier 42, the processing circuit 43 and the A/D converter 44.

Further, the processor 4 has a selector 45, a differential circuit 46 as a differential value calculating section, memories 47a and 47b, a calculation circuit 48 as a calculation section, and the region determining circuit 49 as a region discriminating section, as shown in FIG. 1.

Furthermore, the processor 4 has a white balance circuit 50, an image processing circuit 51 as an image processing section, a D/A converter 52, the timing generator 53 which generates and outputs a timing signal indicating an operation timing, a mode switching circuit 54 which generates and outputs an observation mode switching signal indicating that the observation mode is switched, a dimming control parameter switching circuit 55, and a dimming circuit 56, as shown in FIG. 1.

The selector 45 outputs a white color light image signal as the image signal which is inputted to itself in response to the timing of emission of the white color light to the object, to the white balance circuit 50, based on the input timing of a timing signal. Further, the selector 45 outputs a fluorescence image signal as the image signal inputted to itself in response to the timing of emission of the excitation light to the object, to the differential circuit 46 based on the input timing of a timing signal. Further, the selector 45 outputs the reference light image signal as the image signal inputted to itself in response to the timing of emission of the reference light to the object to the differential circuit 46 based on the input timing of a timing signal.

The differential circuit 46 calculates a fluorescence differential value as an absolute value of a differential value between adjacent pixels based on the fluorescence image signal from the selector 45. The differential circuit 46 updates a storage content of the memory 47a based on the calculated fluorescence differential value.

Meanwhile, the differential circuit 46 calculates a reference light differential value as an absolute value of a differential value between adjacent pixels based on the reference light image signal from the selector 45. The differential circuit 46 updates a storage content of the memory 47b based on the calculated reference light differential value.

The calculation circuit 48 simultaneously reads the fluorescence differential value stored in the memory 47a and the reference light differential value stored in the memory 47b at the timing of update of the storage contents of both the memories 47a and 47b. The calculation circuit 48 generates a determination target image as a division value which is obtained by dividing the fluorescence differential value by the reference light differential value, or a subtraction value obtained by subtracting the reference light differential value from the fluorescence differential value, and outputs the determination target image to the region determining circuit 49.

The region determining circuit 49 applies threshold processing to each of the pixels of the inputted determination target image, and thereby, discriminates between a normal region and an abnormal region in the determination target image. The region determining circuit 49 outputs the pixel information relating to the pixel which is determined as an abnormal region of the determination target image to the image processing circuit 51.

The white balance circuit 50 applies white balance processing to the white color light image signal from the selector 45 in response to the input timing of the timing signal, and outputs the white color light image after being subjected to the white balance processing to the image processing circuit 51.

As the image processing for making the pixel visible, which corresponds to the pixel information outputted from the region determining circuit 49 out of the respective pixels of the white color light image outputted from the white balance circuit 50, the image processing circuit 51 performs color conversion processing of converting the color tone of the pixel into a predetermined color, in response to the input timing of a timing signal. Subsequently, the image processing circuit 51 outputs the white color light image after the color conversion processing to the D/A converter 52. The image processing circuit 51 does not perform the aforesaid color conversion processing when the pixel information is not outputted from the region determining circuit 49.

The D/A converter 52 converts the white color light image outputted from the image processing circuit 51 into an analog video signal and outputs the video signal, in response to the input timing of a timing signal.

The timing generator 53 generates a timing signal based on the synchronous signal from the light source apparatus 3, and thereafter, outputs the timing signal to the CCD driver 41, the amplifier 42, the process circuit 43, the A/D converter 44, the selector 45, the white balance circuit 50, the image processing circuit 51 and the D/A converter 52, respectively.

The mode switching circuit 54 generates an observation mode switching signal based on the instruction signal from the mode switching instruction switch 24, and thereafter, outputs the observation mode switching signal to the rotation filter control circuit 37 and the dimming control parameter switching circuit.

The dimming control parameter switching circuit 55 detects the observation mode of the endoscope system 1 based on the observation mode switching signal outputted from the mode switching circuit 54, and outputs the dimming control parameter based on the detection result to the dimming circuit 56.

The dimming circuit 56 performs for the diaphragm apparatus 33 control or the like for amplifying and regulating the brightness of the image when the image of the object picked up by the endoscope 2 is displayed on the monitor 5 as an image based on the image signal outputted from the process circuit 43 and the dimming control parameter outputted from the dimming control parameter switching circuit 55.

Next, an operation of the endoscope system 1 of the present embodiment will be described.

First, as in the state as shown in FIG. 1, a surgeon or the like connects the endoscope 2 to the light source apparatus 3 and the processor 4, and brings the endoscope system 1 into an initial state by turning on the power supply for each section. In the aforementioned initial state, the endoscope system 1 is set as a white color light observation mode.

The mode switching circuit 54 outputs an observation mode switching signal for informing that the observation mode is a white color light observation mode to the rotation filter control circuit 37.

When the rotation filter control circuit 37 detects that the observation mode is a white color light observation mode based on the inputted observation mode switching signal, the rotation filter control circuit 37 performs control for the rotation filter motor 36 so that the light emitted from the lamp 31 passes through only the white color light filter 34A. Further, the rotation filter control circuit 37 outputs a synchronous signal for indicating that the rotation filter 34 is stopping to the timing generator 53 in the white color light observation mode.

The rotation filter motor 36 adjusts the position of the rotation filter 34 so that only the white color light filter 34A is interposed on the optical path of the lamp 31 based on the control of the rotation filter control circuit 37.

Thereby, the light source apparatus 3 supplies a white color light as the illuminating light in the white color light observation mode to the light guide 6.

The white color light supplied to the light guide 6 illuminates the object such as a biological tissue after passing through the illumination optical system 21.

The reflection light of the aforesaid white color light passes through the objective optical system 22 and the excitation light cut filter 23a to be caused to form an image, and the image is picked up by the CCD 23, and thereafter, is outputted to the processor 4 as an image pickup signal.

The image pickup signal outputted from the CCD 23 is amplified by the amplifier 42, is subjected to correlated double sampling, noise removal and the like by the process circuit 43. The image pickup signal is converted into a digital image signal by the A/D converter 44, and thereafter, is outputted to the selector 45.

Meanwhile, the timing generator 53 keeps outputting the timing signal at a predetermined signal level in the white color light observation mode based on the synchronous signal outputted from the rotation filter control circuit 37. Thereby, the timing signal at the aforesaid predetermined signal level keeps to be inputted in the selector 45.

The selector 45 outputs the image signal outputted from the A/D converter 44 to the white balance circuit 50 in sequence based on the timing signal at the aforesaid predetermined signal level.

The image signal outputted from the selector 45 is subjected to white balance processing by the white balance circuit 50, and after passing through the image processing circuit 51, the image signal is outputted to the monitor 5 while being converted into a video signal by the D/A converter 52.

As a result that the operation described above is performed in the white color light observation mode, the image of the object which shows a color tone substantially equivalent to that of observation by naked eyes is displayed on the monitor 5, as the image of the object in the white color light observation.

Thereafter, when an instruction signal for switching the observation mode of the endoscope system 1 to a fluorescence observation mode from the white color light observation mode is outputted by the mode switching instruction switch 24 being operated, the mode switching circuit 54 outputs an observation mode switching signal for informing that the observation mode is switched to the fluorescence observation mode from the white color light observation to the rotation filter control circuit 37 and the dimming control parameter switching circuit 55.

When the rotation filter control circuit 37 detects that the observation mode is the fluorescence observation mode based on the inputted observation mode switching signal, the rotation filter control circuit 37 performs control for the rotation filter motor 36 so that the light emitted from the lamp 31 sequentially passes through each of the filters of the rotation filter 34. Further, the rotation filter control circuit 37 outputs a synchronous signal synchronized with the rotation of the rotation filter 34 to the timing generator 53 in the fluorescence observation mode.

The rotation filter motor 36 rotates the rotation filter 34 at a predetermined rotational frequency so that the white color light filter 34A, the excitation light filter 34B and the reference light filter 34C are sequentially interposed on the optical path of the lamp 31 based on the control of the rotation filter control circuit 37.

Thereby, the light source apparatus 3 supplies a frame-sequential light configured by a white color light, an excitation light and a reference light to the light guide 6 as the illuminating light in the fluorescence observation mode.

The frame-sequential light supplied to the light guide 6 illuminates the object such as a biological tissue after passing through the illumination optical system 21.

The reflection lights of the white color light and the reference light in the aforesaid frame-sequential light pass through the objective optical system 22 and the excitation light cut filter 23a, are caused to form images, and the images are picked up by the CCD 23, and thereafter, are respectively outputted to the processor 4 as image pickup signals.

Meanwhile, the object is excited by the excitation light in the aforesaid frame-sequential light, and fluorescence is emitted from the object. The fluorescence emitted from the object passes through the objective optical system 22 and the excitation light cut filter 23a, is caused to form an image, and the image is picked up by the CCD 23, and thereafter, is outputted to the processor 4 as an image pickup signal.

The respective image pickup signals outputted from the CCD 23 are amplified by the amplifier 42, are subjected to correlated double sampling, noise removal and the like by the process circuit 43, are converted into digital image signals by the A/D converter 44, and thereafter, are outputted to the selector 45.

Meanwhile, the timing generator 53 outputs a timing signal indicating the operation timing in the fluorescence observation mode based on the synchronous signal outputted from the rotation filter control circuit 37.

The selector 45 outputs the white color light image signal as the image signal inputted to itself in response to the timing of emission of the white color light to the object out of the image signals outputted from the A/D converter 44 to the white balance circuit 50 based on the input timing of the timing signal. Further, the selector 45 outputs the fluorescence image signal as the image signal inputted to itself in response to the timing of emission of the excitation light to the object to the differential circuit 46 based on the input timing of the timing signal. Further, the selector 45 outputs the reference light image signal as the image signal inputted to itself in response to the timing of emission of the reference light to the object to the differential circuit 46 based on the input timing of the timing signal.

The white balance circuit 50 applies white balance processing to the white color light image signal from the selector 45 in response to the input timing of the timing signal, and outputs the white color light image after the white balance processing to the image processing circuit 51.

The differential circuit 46 calculates the fluorescence differential value as shown in FIG. 5, for example, by calculating the absolute value of the differential value between the adjacent pixels in the fluorescence image corresponding to the inputted fluorescence image signal. The differential circuit 46 stores the calculated fluorescence differential value in the memory 47a. Further, the differential circuit 46 calculates the reference light differential value as shown in FIG. 6, for example, by calculating the absolute value of the differential value between the adjacent pixels in the reference light image corresponding to the inputted reference light image signal. The differential circuit 46 stores the calculated reference light differential value into the memory 47b.

The calculation circuit 48 simultaneously reads the fluorescence differential value stored in the memory 47a and the reference light differential value stored in the memory 47b at the timing of update of the storage contents of both the memories 47a and 47b. The calculation circuit 48 generates a determination target image, for example, as shown in FIG. 7 as the division value obtained by dividing the fluorescence differential value by the reference light differential value, or the subtraction value obtained by subtracting the reference light differential value from the fluorescence differential value, and outputs the determination target image to the region determining circuit 49.

Incidentally, the aforementioned fluorescence differential value and reference light differential value include finite values only in the boundary portion with a change in the gradation value, and therefore, have less influence on the change of the total amount of the gradation value due to mucosal extension. According to the present embodiment, by performing division or subtraction between the fluorescence differential value and the reference light differential value, the influence which can be caused by the distance to the distal end surface of the endoscope 2, and the angle formed by the biological tissue and the distal end surface of the endoscope 2 can be corrected.

Therefore, according to the determination target image shown as, for example, FIG. 7, which is generated in the calculation circuit 48, the boundary portion of the abnormal region is extracted.

The region determining circuit 49 discriminates between a normal region and an abnormal region in the determination target image by applying threshold processing to each of the pixels of the inputted determination target image. The region determining circuit 49 outputs the pixel information relating to the pixels determined as an abnormal region in the aforesaid determination target image to the image processing circuit 51.

The image processing circuit 51 performs color conversion processing for converting the color tone of the pixels corresponding to the pixel information which is outputted from the region determining circuit 49, among the respective pixels of the white color light image outputted from the white balance circuit 50, into a predetermined color, in response to the input timing of a timing signal. Subsequently, the image processing circuit 51 outputs the white color light image after the aforesaid color conversion processing into the D/A converter 52.

The D/A converter 52 converts the white color light image outputted from the image processing circuit 51 into an analog video signal and outputs the video signal, in response to the input timing of a timing signal.

As a result that the operation described above is performed in the fluorescence observation mode, the image of the object with a normal region showing the color tone substantially equivalent to the observation by naked eyes, and the boundary portion of the region where a lesion is present showing a predetermined color is displayed on the monitor 5 as the image of the object in the fluorescence observation.

As described above, according to the endoscope system 1 of the present embodiment, the region where a lesion is present can be clearly shown irrespective of the observation conditions in the observation using auto fluorescence.

According to the processor 4 of the present embodiment, the processor 4 is not limited to the one including the configuration which outputs the pixel information outputted from the region determining circuit 49 to the monitor 5 while superimposing the pixel information on the white color light image outputted from the white balance circuit 50 in the fluorescence observation, and may be the one including the configuration which outputs the determination target image generated by, for example, the calculation circuit 48 and the white color light image outputted from the white balance circuit 50 to the monitor 5 by arranging the determination target image and the white color light image side by side.

Further, the calculation circuit 48 of the present embodiment is not limited to the one which performs the aforementioned processing as the processing at the time of generating the determination target image, and may be the one which further performs preprocessing for removing the component corresponding to the random noise which occurs in a dark portion in advance.

In concrete, the calculation circuit 48 may read the fluorescence differential value stored in the memory 47a and the reference light differential value stored in the memory 47b, and thereafter, may perform threshold processing for the respective images, as the aforementioned preprocessing.

The calculation circuit 48 can generate the determination target image in which the component corresponding to the random noise which occurs in a dark portion is not extracted as the boundary portion of an abnormal portion by performing calculation using the fluorescence differential value and the reference light differential value after performing such preprocessing. More specifically, the aforementioned threshold processing is performed in the calculation circuit 48, and thereby extraction precision of an abnormal region can be enhanced.

Further, according to the present embodiment, the calculation circuit 48 is not limited to the one using the division value obtained by dividing the fluorescence differential value by the reference light differential value, or the subtraction value obtained by subtracting the reference light differential value from the fluorescence differential value, at the time of discrimination between a normal region and an abnormal region, and may be the one using the information defining the pixel value in each of the pixels of the fluorescence differential value and the reference light differential value as a vector component.

In this case, the calculation circuit 48 defines the pixel value of one pixel position in the fluorescence differential value, and the pixel value of the one pixel position in the reference light differential value as vector components. Thereafter, the calculation circuit 48 plots the value of the vector of the aforesaid one pixel on the plane with the value of a pixel value $\oplus \Delta T_F|$ in the fluorescence differential value set as an axis of ordinates, and the value of a pixel value $|\Delta T_{Ref}|$ in the reference light differential value set as an axis of abscissa.

Subsequently, the calculation circuit 48 sequentially acquires the values of the aforementioned vectors and plots them on the aforesaid plane in each of the pixel positions of the fluorescence differential value and the reference light differential value, and thereby, acquires the two-dimensional scatter data as shown in FIG. 8, for example. Thereafter, the calculation circuit 48 outputs the aforesaid two-dimensional scatter data to the region determining circuit 49.

Meanwhile, the region determining circuit 49 calculates a magnitude T and a phase D of the value of each of the vectors included in the two-dimensional scatter data outputted from the calculation circuit 48 by using the following expressions (1) and (2).

$$T=(|\Delta T_F|^2+|\Delta T_{Ref}|^2)^{1/2} \tag{1}$$

$$D=\arctan(|\Delta T_F|/|\Delta T_{Ref}|) \tag{2}$$

The region determining circuit 49 regards the vectors which are less than a threshold value $T_0$ of the magnitude, among the values of the respective vectors included in the two-dimensional scatter data as the vectors to which the noise components contributes greatly, and removes such vectors from the discrimination target. Further, the region determining circuit 49 determines the vectors which are below a threshold value $D_0$ of the phase, among the values of the vectors which are not removed from the discrimination target, as the pixels corresponding to the normal region or the boundary portion generated by illumination intensity distribution. Further, the region determining circuit 49 determines the vectors which are equal to or larger than a threshold value $D_0$ of the phase, among the values of the vectors which are not removed from the discrimination target, as the pixels corresponding to an abnormal region. Subsequently, the region determining circuit 49 outputs the information as shown in FIG. 9, for example, which is obtained as the discrimination result by a series of processes so far, to the image processing circuit 51 as the pixel information. The following processing is similar to the processing already described, and therefore, the explanation will be omitted.

Here, the aforementioned threshold value $T_0$ of the magnitude and the threshold value $D_0$ of the phase are desirably set so that the identification probability of a lesion region and an artifact becomes the highest by statistically analyzing the data acquired in advance with biological tissues as the target.

Further, the aforementioned vector is defined as a two-dimensional vector using the pixel value of one kind of reference light differential value, but the vector is not limited thereto, and may be the vector which is defined as the vector of three dimensions or more using the pixel values of a plurality of kinds of reference light differential values differing from each other and corresponding to the number of reference lights emitted to the object.

As described above, by using the information defining the pixel value in each of the pixels of the fluorescence differential value and the reference light differential value as the vector component at the time of discrimination between a normal region and an abnormal region, the abnormal region and the other regions can be separated based on the phase of the vector while contribution by a noise component is removed based on the magnitude of the vector, and as a result, extraction precision of an abnormal region can be enhanced.

The present embodiment is not limited to the application to the image pickup system with the configuration as described above, but may be applied to the image pickup system with the configuration including, for example, an endoscope having a monochrome CCD, and a light source apparatus capable of emitting a frame-sequential light configured by an R (red) light, a G (green) light and a B (blue) light, and a frame-sequential light configured by a white color light, a reference light and an excitation light. Further, the present embodiment may be the one applied to the image pickup system with the configuration including, for example, an endoscope having a color CCD, and a light source apparatus capable of emitting a frame-sequential light configured by an R light, a G light and a B light, and a frame-sequential light configured by an R light, a reference light and an excitation light.

The present invention is not limited to the aforementioned embodiment, and various modifications and applications can be made within the range without departing from the gist of the invention as a matter of course.

What is claimed is:

1. An endoscope system, comprising:
   a light source apparatus that emits an excitation light and a reference light to a biological tissue;
   an endoscope including an image pickup device that picks up images of reflection lights, which are fluorescence emitted from the biological tissue in response to the excitation light, and the reference light that are reflected in the biological tissue, and outputs the images as image pickup signals respectively;
   an image generating section that generates a fluorescence image corresponding to the fluorescence, and a reference light image corresponding to the reflection light respectively based on the image pickup signals;
   a differential value calculating section that calculates a fluorescence differential value as a differential value corresponding to the fluorescence image, and a reference light differential value as a differential value corresponding to the reference light image respectively;
   a calculation section that performs calculation processing for acquiring a pixel value of one pixel position in the fluorescence differential value, and a pixel value of the one pixel position in the reference light differential value as vector components, by using the fluorescence differential value and the reference light differential value; and
   a region discriminating section that discriminates between an abnormal region and a normal region in the biological tissue by applying threshold processing to each of a magnitude and a phase of the vector obtained as a calculation result of the calculation section.

2. The endoscope system according to claim 1, further comprising an image processing section that performs image processing for making the abnormal region in the biological tissue visible based on a discrimination result of the region discriminating section.

3. The endoscope system according to claim 1, wherein the region discriminating section determines that the abnormal region is present at the one pixel position when it is detected that the magnitude of the vector is a predetermined first threshold value or more, and the phase of the vector is a predetermined second threshold value or more.

* * * * *